(12) United States Patent
Chang et al.

(10) Patent No.: US 10,934,314 B1
(45) Date of Patent: Mar. 2, 2021

(54) METHOD FOR PREPARING ORGANOBORON DERIVATIVE CONTAINING OXYGEN AND AROMATIC RING AS LABELED PRECURSOR OF DOPAMINE POSITRON EMISSION TOMOGRAPHY IMAGING AGENT

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Yu Chang, Taoyuan (TW); Wen-Ching Wu, Taoyuan (TW)

(73) Assignee: Institute of Nuclear Energy Research, Atomic Energy Council, Executive Yuan, R.O.C., Taoyuan (TW)

( * ) Notice: Subject to any disclaimer, the term of this patent is extended or adjusted under 35 U.S.C. 154(b) by 0 days.

(21) Appl. No.: 16/994,860

(22) Filed: Aug. 17, 2020

(30) Foreign Application Priority Data

Oct. 31, 2019 (TW) ................................. 108139508

(51) Int. Cl.
| | | |
|---|---|---|
| *C07F 5/02* | (2006.01) | |
| *G01N 33/60* | (2006.01) | |
| *B01D 11/02* | (2006.01) | |
| *B01D 15/08* | (2006.01) | |

(52) U.S. Cl.
CPC .............. *C07F 5/02* (2013.01); *B01D 11/028* (2013.01); *B01D 11/0288* (2013.01); *B01D 15/08* (2013.01); *G01N 33/60* (2013.01); *G01N 2800/2835* (2013.01)

(58) Field of Classification Search
None
See application file for complete search history.

(56) References Cited

PUBLICATIONS

Moore, James M., Detection of Ecgonine in Urine. Clinical Chemistry (1975), 21(10), pp. 1538 and 1540.*

* cited by examiner

*Primary Examiner* — Brian J Davis
(74) *Attorney, Agent, or Firm* — Rosenberg, Klein & Lee

(57) ABSTRACT

A method for preparing organoboron derivatives containing oxygen atoms and an aromatic ring as labeled precursors of dopamine positron emission tomography imaging agents is revealed. Hydrochloride salt of cocaine is used as an initiator. Organoboron derivatives containing oxygen atoms are directly produced on an aromatic ring as drug substances and the aromatic ring is directly labeled with radioisotope fluorine-18 (F-18). The method takes only five steps including four steps for preparing organoboron derivatives containing oxygen atoms and an aromatic ring as drug substances and a step of labeling the aromatic ring of the organoboron derivatives with F-18 directly. Not only the process time is significantly reduced, the total yield rate is also improved effectively.

3 Claims, 4 Drawing Sheets

METHOD FOR PREPARING ORGANOBORON DERIVATIVE CONTAINING OXYGEN AND AROMATIC RING AS LABELED PRECURSOR OF DOPAMINE POSITRON EMISSION TOMOGRAPHY IMAGING AGENT

BACKGROUND OF THE INVENTION

Field of the Invention

The present application relates to a method for preparing labeled precursors of dopamine positron emission tomography imaging agents, especially to a method for preparing organoboron derivatives containing oxygen atoms and an aromatic ring as labeled precursors of dopamine positron emission tomography imaging agents.

Description of Related Art

Cocaine and its analogues have high affinity for the dopamine transporter. Derivatives synthesis by using cocaine as an initiator and labeled with radionuclides can be used as dopamine transporter imaging agents being applied to diagnosis of Parkinson's disease in the elderly and illness of the elderly. The Institute of Nuclear Energy Research (INER) has developed an $N_2S_2$ ligand, such as TRODAT-1 which has been chelated with radioisotope-Tc-99m for many years. A type of drug TRODAT-1 is labeled with Tc-99m to get a freeze-dried product Tc-99m-TRODAT-1 which is used to get single-photon emission computed tomography (SPECT) images of patient's lesions. Now this agent has been widely used in diagnostic radiology, neurology, and medical imaging examinations in hospitals at home and abroad.

However, a conventional method for synthesis of drug substance TRODAT-1 takes eleven steps and the manufacturing process is complicated. In a part of the steps, the yield rate is lower due to the formation of isomeric by-products. This causes great challenges in the yield rate and the stability. Therefore, it is an important point, how to overcome above issues. A new type of labeled precursor of dopamine transporter imaging agents has been developed by the modification of the molecular structure of cocaine for providing a better molecular skeleton to bind to dopamine transporters. At the same time, a new functional group used for being connected with suitable radioisotopes has been developed. Thus, both the sensitivity of the imaging and the yield rate of the drug substances are improved and this creates a new pathway for synthesis of radiopharmaceuticals for the diagnosis of Parkinson's disease.

SUMMARY OF THE INVENTION

Therefore, it is a primary object of the present application to provide a method for preparing organoboron derivatives containing oxygen atoms and an aromatic ring as labeled precursors of dopamine positron emission tomography imaging agents with fewer production steps.

It is another object of the present application to provide a method for preparing organoboron derivatives containing oxygen atoms and an aromatic ring as labeled precursors of dopamine positron emission tomography imaging agents in which the aromatic ring has stable covalent bond while being labeled with radioisotope F-18.

BRIEF DESCRIPTION OF THE DRAWINGS

The structure and the technical means adopted by the present application to achieve the above and other objects can be best understood by referring to the following detailed description of the preferred embodiments and the accompanying drawings, wherein.

DETAILED DESCRIPTION OF THE PREFERRED EMBODIMENT

In order to learn features and functions of the present application, please refer to the following embodiments with detailed description.

The present method is for synthesis of organoboron derivatives containing oxygen atoms and an aromatic ring. Cocaine Hydrochloride (cocaine HCl) is used as an initiator because cocaine has high affinity for the dopamine transporter. Compared with synthesis of TRODAT-1 raw materials by a conventional method, the present organoboron derivatives containing oxygen atoms and an aromatic ring are synthesized by modification of cocaine, connection with an aromatic ring and direct formation of organoboron derivatives containing oxygen atoms on the aromatic ring. Then the aromatic ring is directly labeled with radioisotope fluorine-18 (F-18). During synthesis of TRODAT-1, additional seven steps are carried out for connection with an $N_2S_2$ structure after being connected with the aromatic ring in order to be labeled with Tc-99m. For being labeled with Tc-99m by coordinate bonds, the synthesis of TRODAT-1 takes up to eleven steps. The production process takes a long time no matter small quantity in laboratory or process scale-up and technology transfer, and the yield rate is unable to be improved due to the multiple steps. The present synthesis method in which organoboron derivatives containing oxygen atoms are directly formed on the aromatic ring and the aromatic ring is labeled with radioisotope F-18 only takes five steps, including four steps for preparing drug substances of the organoboron derivatives containing oxygen atoms and an aromatic ring and one step of labeling the aromatic ring of the organoboron derivatives with F-18. Thereby the process time is significantly reduced and the yield rate is effectively increased.

Figure 1:
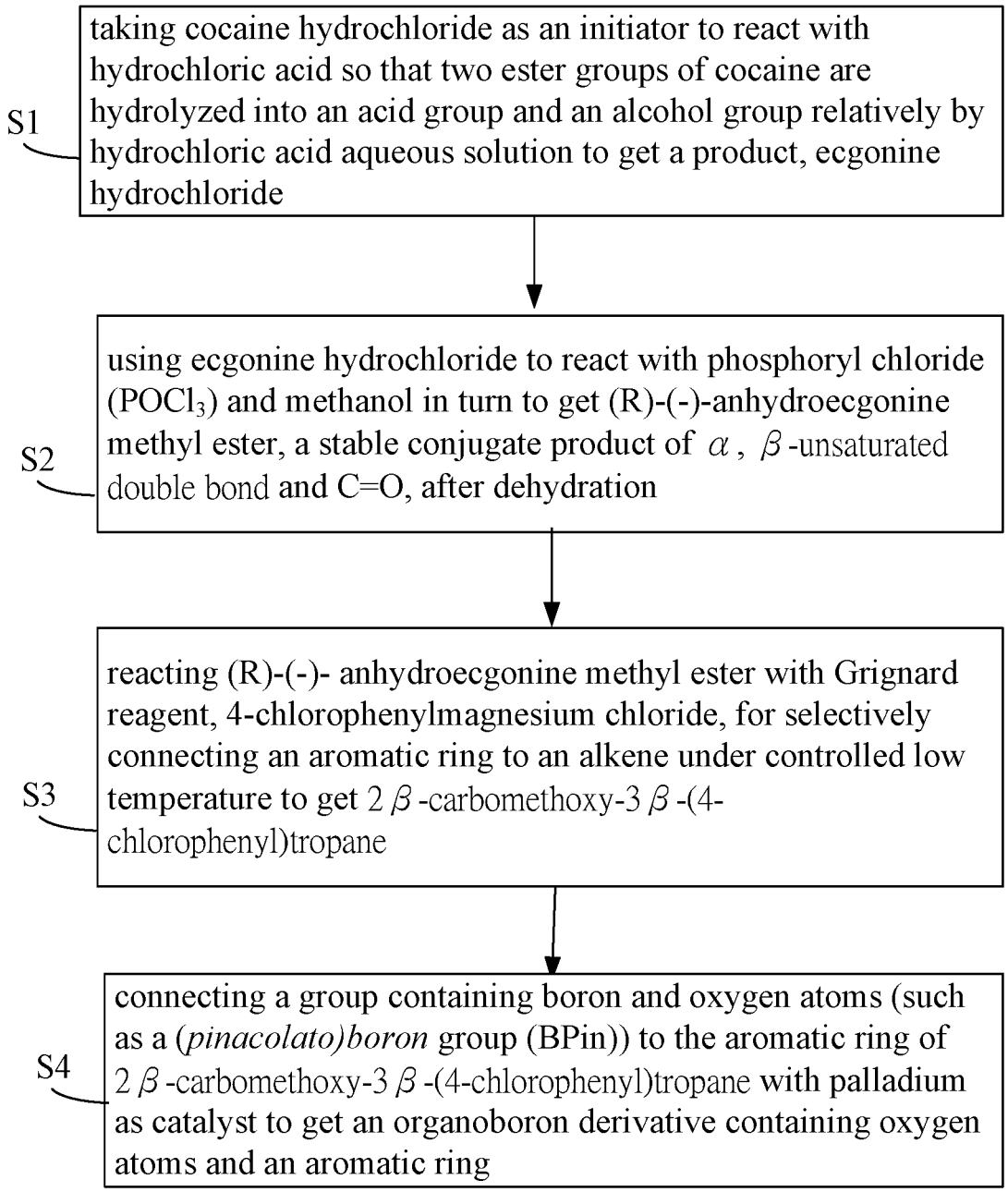
FIG. 1 is a flow chart showing steps of an embodiment according to the present application.

Refer to FIG. 1, a flow chart showing steps of an embodiment according to the present application is revealed. A method for preparing organoboron derivatives containing oxygen atoms and an aromatic ring as precursor for labeling dopamine positron emission tomography imaging agents according to the present application includes the following steps:

step S1: taking cocaine hydrochloride as an initiator to react with hydrochloric acid so that two ester groups of cocaine are hydrolyzed into an acid group and an alcohol group relatively by hydrochloric acid aqueous solution to get a product, ecgonine hydrochloride;

step S2: using ecgonine hydrochloride to react with phosphoryl chloride ($POCl_3$) and methanol in turn to get (R)-(−)-anhydroecgonine methyl ester, a stable conjugate product of α,β-unsaturated double bond and C=O, after dehydration;

step S3: reacting (R)-(−)-anhydroecgonine methyl ester with Grignard reagent, 4-chlorophenylmagnesium chloride, for selectively connecting an aromatic ring to an alkene under controlled low temperature to get 2β-carbomethoxy-3β-(4-chlorophenyl)tropane; and step S4: connecting a group containing boron and oxygen atoms (such as a (pinacolato) boron group (BPin)) to the aromatic ring of 2β-carbomethoxy-3β-(4-chlorophenyl)tropane with palladium as catalyst to get an organoboron derivative containing oxygen atoms and an aromatic ring.

Moreover, the aromatic ring of the above organoboron derivative is directly labeled with radioisotope fluorine-18 (F-18) whose atomic size is close to that of hydrogen. There is almost no difference between the structure before the labeling and the structure after the labeling and the covalent bond is more stable.

Figure 2:
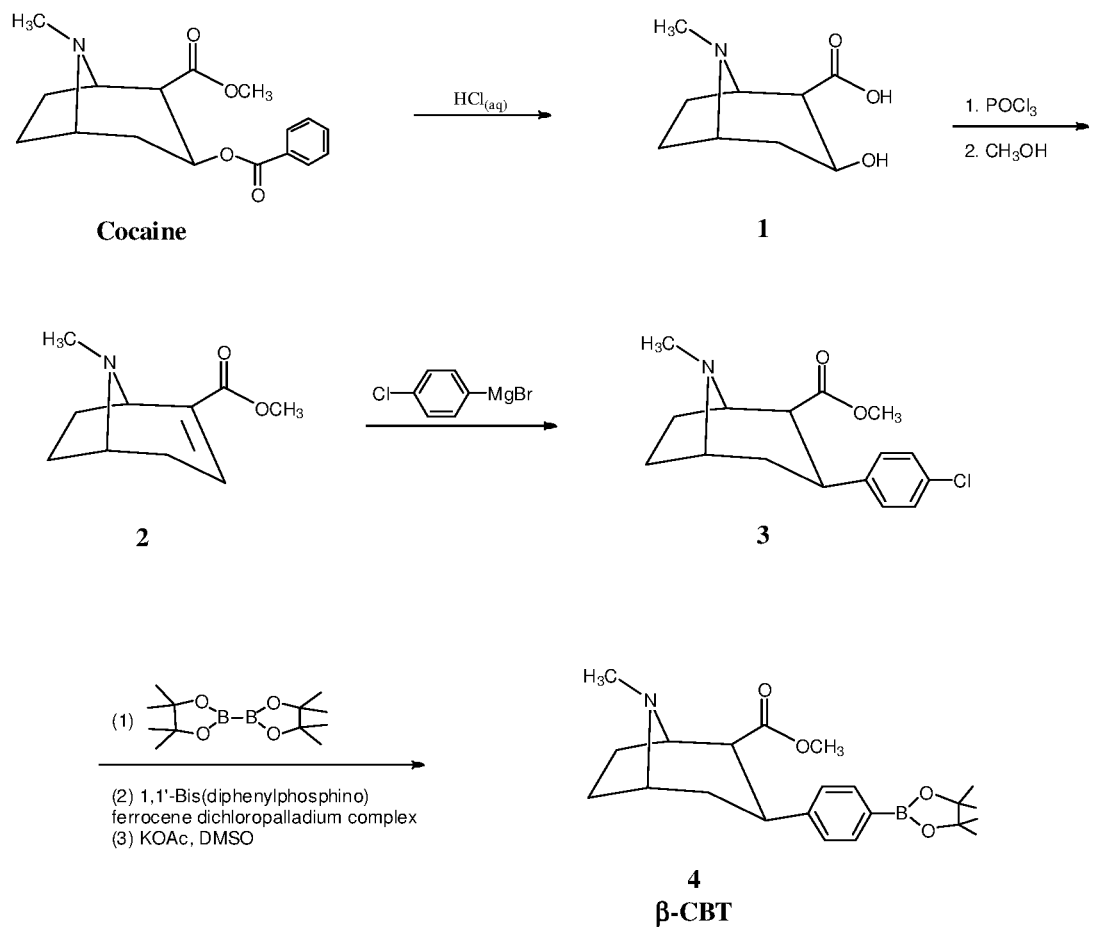
FIG. 2 is a synthetic pathway of an embodiment according to the present application.

Refer to FIG. 2, a synthetic pathway of an embodiment according to the present application is revealed.

Place 30 g (89 mmol) hydrochloride salt of cocaine (cocaine HCl) and 500 ml 0.8 N HCl aqueous solution into a 1 L round-bottom flask and heat under reflux at 105° C. for 20 hours. After being reacted, cool reaction solution by an ice bath and stir the reaction solution for 30 minutes. Then while solid is precipitated after the reaction solution is cooled down to room temperature. After vacuum filtration, get a filtrate and extract the filtrate with ether (3×500 mL). Remove the organic phase and concentrate the aqueous phase under vacuum at 80° C. The crude product obtained is combined with the above white solid, washed with dichloromethane ($CH_2Cl_2$) and filtered under vacuum to get a product, 19.26 g (87.6 mmole) compound 1, and the yield rate is 98.42%.

IR (KBr): ν 3284 (O—H), 1701 (C=O) $cm^{-1}$ $^1$H NMR ($CD_3OD$) δ(ppm): δ4.35 (m, 1H), 4.10 (d, 1H), 3.88 (m, 1H), 3.15 (dd, 1H), 2.82 (s, 3H, NC$\underline{H}_3$), 2.36 (m, 2H), 2.10 (m, 3H)

$^{13}$C NMR ($CD_3OD$) δ(ppm): δ176.79 (C=O), 65.82, 64.70, 61.46, 49.00, 39.23 (N$\underline{C}H_3$), 36.86, 24.92, 24.19

Synthesis of anhydroecgonine methyl ester: add 19 g (86.4 mmol) compound 1 into 100 mL phosphoryl chloride and heat under reflux at 110° C. for 3 hours. Remove excess phosphoryl chloride ($POCl_3$) by distillation under reduced pressure and dry in vacuum at 1 torr for 24 hours. The crude intermediate product obtained by vacuum drying is added into 100 mL anhydrous methanol ($CH_3OH$) in ice bath. After being dissolved completely, stir the solution at room temperature for 5 hours. After completing the stirring, remove excess methanol by distillation under reduced pressure and dissolve residue in 100 mL water. Adjust pH value of the solution to 7 with 1N sodium hydroxide aqueous solution and extract with ether (3×100 mL) Each time remove the organic layer and adjust pH value of the aqueous layer to 10-12 with 1N sodium hydroxide aqueous solution. Then extract the combined aqueous layers with ether (3×100 mL) again. The organic layer is separated, dried with anhydrous sodium sulfate, and concentrated under vacuum to get a compound 2, 14.44 g (80.3 mmol) anhydroecgonine methyl ester, and the yield rate is 92.94%.

IR (KBr): ν 1730 (C=O) $cm^{-1}$ $^1$H NMR ($CDCl_3$) δ 6.81 (m, 1H), 3.98 (d, J=5.6 Hz, 1H), 3.94 (s, 3H, OC$\underline{H}_3$), 3.45 (m, 1H), 2.83 (d, br, J=19.8 Hz, 1H), 2.54 (s, 3H, NC$\underline{H}_2$), 2.36 (m, 2H), 2.04 (m, 2H), 1.72 (m, 1H)

$^{13}$C NMR ($CDCl_3$) δ 173.10 (C=O) 166.12, 135.81, 58.10, 56.32, 51.06 (O$\underline{C}H_3$), 36.00 (N$\underline{C}H_3$), 34.01, 31.66, 29.88

Synthesis of 2β-carbomethoxy-3β-(4-chlorophenyl)tropane: dissolve 14 g (78 mmol) compound 2 in 50 mL anhydrous dichloromethane. Also dissolve 160 mL (160 mmol) 4-chlorophenyl magnesium bromide 1M solution in diethyl ether (Grignard reagent) into 950 mL anhydrous dichloromethane, cool down to −50° C. and introduce nitrogen gas. Then drop the former solution slowly into the later solution and keep the temperature at about −50° C. during the drop process. Stir the mixture for 3 hours and cool down to −78° C. Then add a mixture of trilfluoroacetic acid (12.3 mL, 0.160 mol) and anhydrous dichloromethane (25 mL) and stir for 30 minutes. After completing stirring and the temperature turning back to room temperature, add about 1 L pure water and acidify the aqueous phase to pH 1.0-2.0 with hydrochloric acid. Then separate the two phases, remove the organic phase, and alkalize the aqueous phase to pH 11.0-12.0 with saturated sodium hydroxide aqueous solution (3×200 mL) Next extract with ethyl acetate (3×1 L) and use a centrifuge to separate the two phases. The organic phase is dried with anhydrous sodium sulfate and concentrated under vacuum to get a crude product of compound 3. The crude product is separated and purified by liquid column chromatography ($SiO_2$, EtOAc) to get 10.16 g (34.7 mmol) compound 3, 2β-carbomethoxy-3β-(4-chlorophenyl)tropane, and the yield rate is 44.46%.

IR (KBr) ν 1732 (C=O) $cm^{-1}$ $^1$H NMR($CD_3OD$) δ(ppm): 1.64 (m, 4H, two —$CH_2$), 2.20 (t, 2H, N=C—$CH_2$), 3.10 (t, 2H, C=N—$CH_2$), 3.35 (dd, 2H, —$CH_2$), 3.82 (s, 3H, —$OCH_3$), 3.95 (t, 2H, —$CH_2$), 4.00 (dd, 2H, —$CH_2$), 4.12 (t, 2H, —$CH_2$), 6.62 (s, 1H), 6.75 (d, 1H), 7.55 (d, 1H), 7.70 (dd, 1H), 8.15 (d, 1H), 8.63 (d, 1H), 9.15 (d, 2H)

$^{13}$C NMR ($CD_3OD$) δ(ppm): 173.5, 166.5, 163.1, 151.0, 148.9, 146.1, 145.5, 134.2, 127.8, 127.3, 117.3, 108.1, 99.7, 71.3, 61.4, 56.7, 45.9, 25.4, 20.8

Synthesis of 2β-Carbomethoxy-3β-(4-pinacolborylphenyl)tropane (β-CBT): dissolve 4 g (13.65 mmol) compound 3, 10 g (39.38 mmol) bis(pinacolato)diboron ($B_2Pin_2$), 0.25 g (0.25 mmol) tris(dibenzylideneacetone)dipalladium(0) ($Pd_2dba_3$), 0.26 g (0.55 mmol) 2-dicyclohexylphosphino-2', 4',6'-triisopropyl biphenyl (XPhos), and 4 g (40.95 mmol) potassium acetate in 30 mL anhydrous 1,4-dioxane and heat under reflux at 110° C. for 3 hours. The reaction solution is cooled down to room temperature and concentrated under reduced pressure. Add and dissolve concentrated solution in dichloromethane and then filter with celite (diatomaceous earth) and wash the filtrate with water for three times. Dry the organic phase with anhydrous sodium sulfate and concentrate under vacuum to get a crude product of compound 4 (β-CBT). The crude product is separated and purified by liquid column chromatography ($SiO_2$, DCM:EA=5:1) to get 0.56 g (7.34 mmol) white solid product, the compound 4 (β-CBT), and the yield rate is 53.8%).

IR(KBr) ν 1746 (C=O) $cm^{-1}$ $^1$H NMR ($CDCl_3$) δ 7.78 (d, 2H, $C_6H_4$), 7.32 (d, 2H, $C_6H_4$), 3.59 (m, 1H, NC$\underline{H}$), 3.43 (s, 3H, OC$\underline{H}_3$), 3.35 (m, 1H, NCH), 3.01 (td, 1H, C$\underline{H}C_6H_4$), 2.96 (dd, 1H, C$\underline{H}CO_2CH_3$), 2.58 (td, 1H, C$\underline{H}_2CHC_6H_4$), 2.21 (s, 3H, NC$\underline{H}_3$), 2.20-1.96 (m, 2H, C$\underline{H}_2CH_2$), 1.78-1.48 (m, 3H, C$\underline{H}_2C\underline{H}_2$), 1.34 (s, 12H, BOC(C$\underline{H}_3)_2$)

$^{13}$C NMR ($CDCl_3$) δ172.80 (C=O), 147.21, 135.17, 127.25 and 84.26 ($C_6H_4$), 66.02 and 62.91 (N$\underline{C}H$), 53.38 ($\underline{C}HCO_2$), 51.87 ($CO_2\underline{C}H_3$), 42.06 (N$\underline{C}H_3$), 34.50 ($\underline{C}HC_6H_4$), 30.37 ($\underline{C}H_2CHC_6H_4$), 26.60 and 25.81 ($\underline{C}H_2\underline{C}H_2$), 25.55 (BO$\underline{C}(CH_3)_2$), 25.48 (BOC($\underline{C}H_3)_2$)

Figure 3:
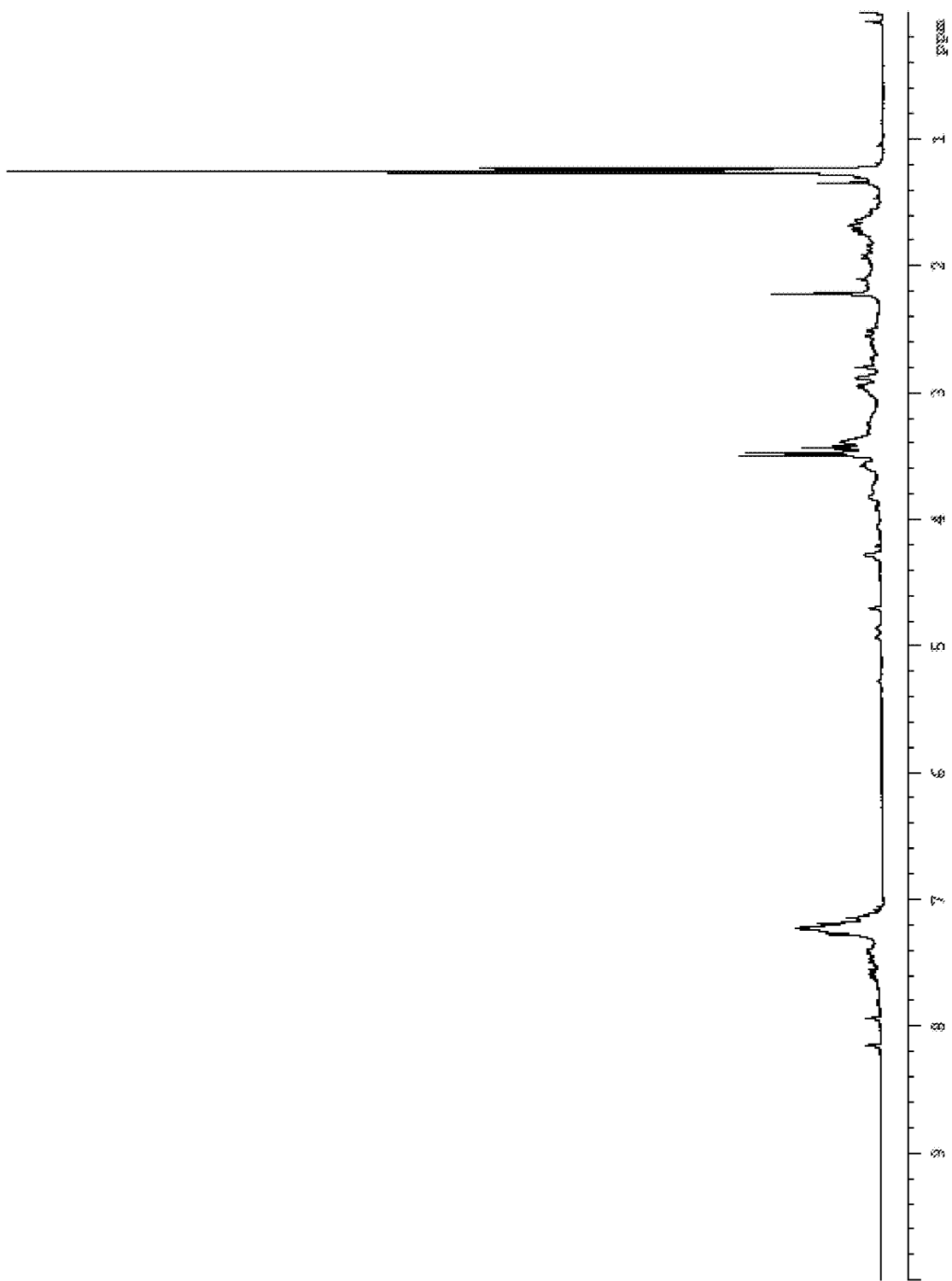
FIG. 3 is $^1$H-NMR spectrum of an embodiment in which β-CBT is not purified by celite according to the present application.
Figure 4:
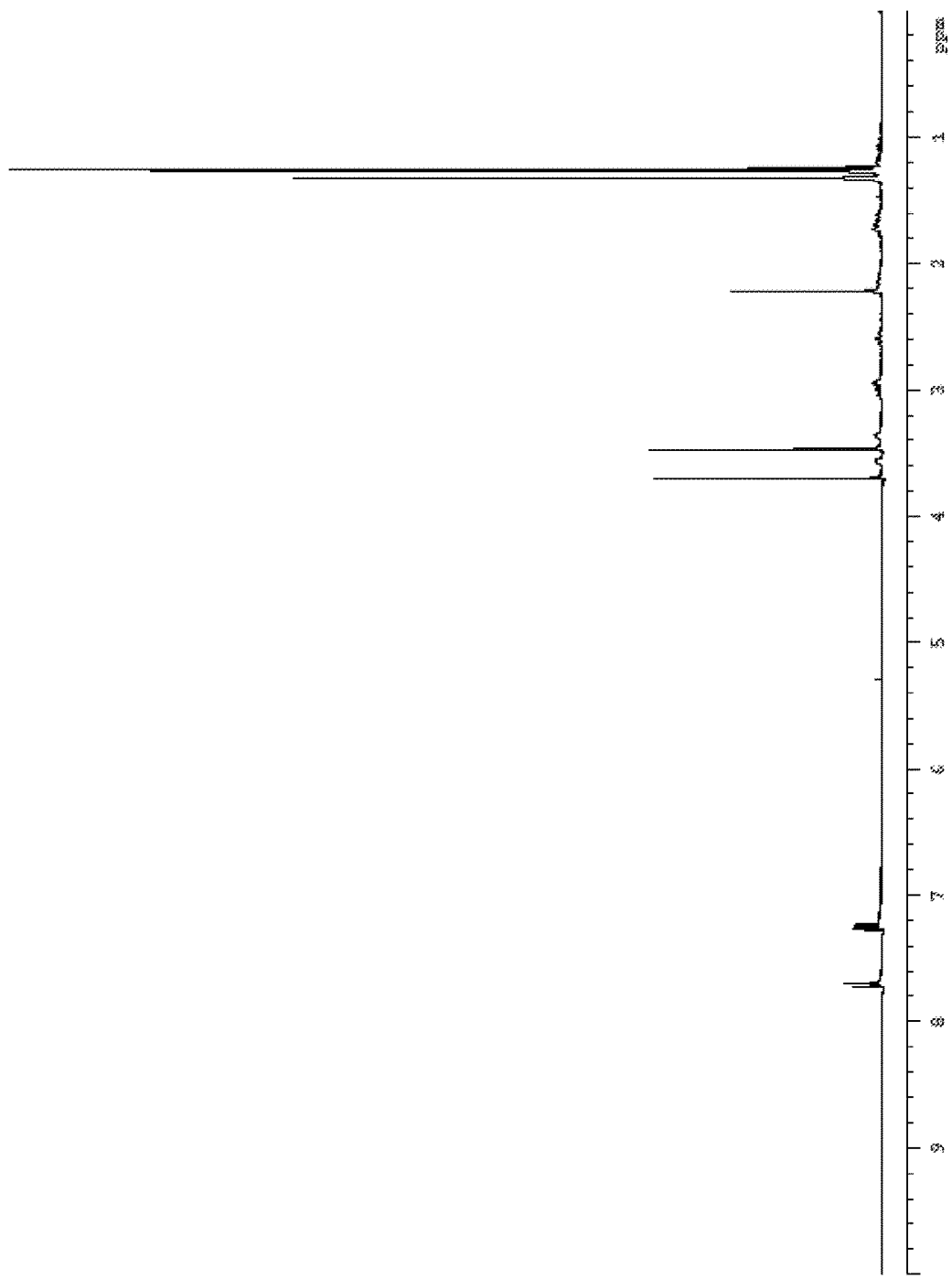
FIG. 4 is $^1$H-NMR spectrum of an embodiment before column purification of β-CBT according to the present application.

During purification of β-CBT, residual $Pd_2dba_3$ and XPhos are absorbed by celite and this can be confirmed by removal of Pd$_2$dba$_3$ and XPhos related signals at 7.3-8.2 ppm in the $^1$H-NMR spectrum (with reference to FIG. 3 showing $^1$H-NMR spectrum of an embodiment in which β-CBT is not purified by celite). Excess potassium acetate and potassium chloride salts generated during the reaction are removed by extraction with dichloromethane and water. Then isolate excess B$_2$Pin$_2$ by column purification. This is also confirmed by removal of B$_2$Pin$_2$ related signals at 1.23 ppm in the $^1$H-NMR spectrum (with reference to FIG. 4 showing $^1$H-NMR spectrum of an embodiment before column purification of β-CBT).

In summary, a method for preparing organoboron derivatives containing oxygen atoms and an aromatic ring as labeled precursors of dopamine positron emission tomography imaging agents according to the present application uses hydrochloride salt of cocaine as an initiator and four steps are carried out for synthesis of β-CBT. Hydrochloride salt of cocaine is hydrolysis in hydrochloric acid solution to get the compound 1. Then the compound 2 is obtained after acyl chlorination, methyl esterification and dehydration. The compound 3 is formed by the reaction of Grignard reagent. Lastly β-CBT is obtained after the compound 3 reacting with B$_2$Pin$_2$. The total yield rate is 21.9%.

β-CBT has two chiral carbon centers so that there are four ($2^2$=4) theoretically possible isomers (2α,3α; 2β,3α; 2α,3β; 2β,3β). In the step S3, chlorobenzene connected to C3 chiral center of tropane is a macromolecular functional group. Owing to steric effect, chlorobenzene can only be connected to the equatorial (β) position, not the axial (α) position. As to another chiral center C2, there are two stereoisomers- alpha (α) and beta (β) isomers generated this step. Thus there are actually two isomers obtained in the steps S3 (2α, 3β and 2β, 3β).

The above two isomers can be isolated and purified by liquid chromatography. In the experiment, the isomer (2β, 3β) is first precipitated and the two isomers, (2α,3β) and (2β,3β), can be isolated and purified smoothly when the stationary phase is silica gel and the mobile phase (eluent) is ethyl acetate.

In the compounds derived from tropane, a isomer (2α,3β) provides no imaging effect after entering human bodies while β isomer has imaging effect. Thus the two isomers, α isomer and β isomer should be isolated and purified effectively, without affecting the following effect of radiopharmaceuticals for imaging.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A method for preparing organoboron derivatives containing oxygen atoms and an aromatic ring as labeled precursors of dopamine positron emission tomography imaging agents comprising the steps of:
   taking cocaine hydrochloride as an initiator to react with hydrochloric acid so that two ester groups of the cocaine are hydrolyzed into an acid group and an alcohol group by the hydrochloric acid to get a product, ecgonine hydrochloride;
   using ecgonine hydrochloride to react with phosphoryl chloride (POCl$_3$) and methanol in turn to get (R)-(−)-anhydroecgonine methyl ester, a stable conjugate product of α,β-unsaturated double bond and C=O, after dehydration;
   reacting (R)-(−)-anhydroecgonine methyl ester with Grignard reagent, 4-chlorophenylmagnesium chloride, for selectively connecting an aromatic ring to an alkene under controlled low temperature to get 2β-carbomethoxy-3β-(4-chlorophenyl)tropane; and
   connecting a group containing boron and oxygen atoms to the aromatic ring of 2β-carbomethoxy-3β-(4-chlorophenyl)tropane with palladium as catalyst to get an organoboron derivative containing oxygen atoms and an aromatic ring.

2. The method as claimed in claim 1, the method further includes a step of directly labeling the aromatic ring of the organoboron derivative containing oxygen atoms and an aromatic ring with radioisotope fluorine-18 (F-18).

3. The method as claimed in claim 1, the method further includes a step of purifying the organoboron derivative containing oxygen atoms and an aromatic ring which includes the steps of:
   absorbing residual tris(dibenzylideneacetone)dipalladium (0)(Pd$_2$dba$_3$) and 2-dicyclohexylphosphino-2',4',6'-triisopropyl biphenyl (XPhos) by diatomaceous earth (celite); and
   removing excess potassium acetate and potassium chloride salts generated during reaction by extraction with dichloromethane and water and then isolating excess bis(pinacolato)diboron (B$_2$Pin$_2$) by column purification.

* * * * *